(12) United States Patent
Chung et al.

(10) Patent No.: US 6,346,617 B1
(45) Date of Patent: *Feb. 12, 2002

(54) CRYSTALLINE 2-HYDROXYMETHYL CARBAPENEM INTERMEDIATE COMPOUNDS AND PROCESS FOR SYNTHESIS THEREOF

(75) Inventors: John Y. Chung, Edison; Nobuyoshi Yasuda, Mountainside; Johnnie L. Leazer, Jr., Metuchen; Mark S. Jensen, Holmdel; Kenneth M. Wells, Neshanic Station; Chunhua Yang, Edison, all of NJ (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/334,397

(22) Filed: Jun. 16, 1999

Related U.S. Application Data (63) Continuation of application No. 09/129,205, filed on Jul. 27, 1998, now abandoned.
(60) Provisional application No. 60/056,967, filed on Aug. 26, 1997.

(51) Int. Cl.[7] .................. C07D 477/14; C07D 477/18; C07F 7/18
(52) U.S. Cl. ...................................... 540/302
(58) Field of Search ......................... 540/302

(56) References Cited

U.S. PATENT DOCUMENTS 4,960,879 A  10/1990  Kyoto ................ 540/302

FOREIGN PATENT DOCUMENTS

EP  0 476 649 A2  3/1992

OTHER PUBLICATIONS

Y. Nagao et al., *J. Org. Chem*, 57, p 4243–4349 (1992).
S. M. Schmitt et al. *J. Antibiotic*, 41(6), p. 780–787 (1988).

*Primary Examiner*—Mark L Berch
(74) *Attorney, Agent, or Firm*—Sylvia A. Ayler; Mark R. Daniel (57) ABSTRACT

A process for preparation of a compound of formula I:

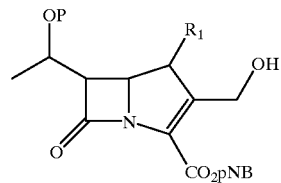

wherein:
$R_1$ represents $CH_3$ or H; and P represents a protecting group;
comprising reacting a compound of formula IV:

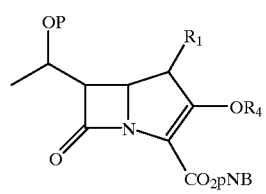

wherein $R_1$ and P and are defined above and $R_4$ represents triflate or $SO_2F$;
in the presence of a catalyst and $(R_3)_3SnCH_2OP''$, wherein each $R_3$ represents $C_{1-4}$ lower alkyl, and P'' represents H or a protecting group, to yield the compound of formula I.

22 Claims, 2 Drawing Sheets

CRYSTALLINE 2-HYDROXYMETHYL CARBAPENEM INTERMEDIATE COMPOUNDS AND PROCESS FOR SYNTHESIS THEREOF

This application is a Continuation application of U.S. application Ser. No. 09/129,205, filed Jul. 27, 1998 now abandoned, which claims the benefit of U.S. Provisional Application No. 60/056,967, filed Aug. 26, 1997.

BACKGROUND OF THE INVENTION

The present invention relates to intermediate compounds useful in the synthesis of carbapenem antibiotics. The carbapenems derived from the present invention are useful against gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). There is an increasing need for carbapenems effective against such pathogens, as well as intermediates which facilitate their production. The intermediates of the present invention thus facilitate an important contribution to therapy for treating infections caused by these difficult to control pathogens.

Prior syntheses of similar intermediate compounds have relied on time-consuming, multi-step reaction protocols, and have generated the intermediate as an unstable oil. See, e.g., U.S. Pat. No. 4,960,879, Shionogi & Co. Ltd. The present invention responds to the need for a more facile synthesis yielding novel, more stable carbapenem intermediates.

SUMMARY OF THE INVENTION

The present invention relates to a process for preparation of a compound of formula I:

wherein:
$R_1$ represents $CH_3$ or H; and P represents a protecting group;
comprising reacting a compound of formula IV:

wherein $R_1$ and P and are defined above and $R_4$ represents triflate or $SO_2F$;
in the presence of a catalyst and $(R_3)_3SnCH_2OP''$, wherein: each $R_3$ represents $C_{1-4}$ lower alkyl, and P'' represents H or a protecting group, to yield the compound of formula I.

This one-vessel process is a more efficient and facile pathway than the traditional multi-step synthesis for preparation of carbapenem intermediates.

The present invention also relates to the compound of formula I:

wherein:
$R_1$ represents $CH_3$ or H; and P and P' independently represent H or a protecting group. This novel compound is a stable and storable crystalline solid.

BRIEF DESCRIPTION OF THE DRAWINGS

The invention is described in connection with the following drawings in which.

DETAILED DESCRIPTION OF THE INVENTION

In one embodiment of the invention, a process for synthesizing a compound of formula I is described:

wherein:
wherein $R_1$ represents $CH_3$ and P represents TES, TMS or TBS; comprising:
reacting a compound of formula IV:

wherein P and $R_1$ are defined above;
in the presence of $ZnCl_2$, $Pd(dba)_2$, and $(R_3)_3SnCH_2OP''$, wherein:
$R_3$ represents a $C_{1-4}$ lower alkyl, and P'' represents H, TES, TMS or TBS; to yield the compound of formula I.

In another embodiment of the invention, a process for synthesizing a compound of formula I is described:

I wherein $R_1$ represents $CH_3$ or H and P represents a protecting group, comprising:

step (1) heating a compound of formula II:

II wherein $R_1$ and P are defined above;
in the presence of wherein $R_2$ is $C_{1-15}$ alkyl, to yield a compound of formula III:

III wherein $R_1$ and P are defined above;

Compound II is commercially available where P is H and $R_1$ is methyl or H. Compound II may also be synthesized according to the general methods disclosed in, for example, Nagao, et al., JOCEAH; J. Org. Chem., EN; 57; 15; 1992; 4243–4249; see also Schmitt, et al., J. Antibiotics 41(6):780–787 (1988).

A lewis acid may be added to the reaction mixture in this first step as an optional reagent. A preferred aspect of the invention is realized when a Lewis acid is employed. Suitable Lewis acids are described below.

step (2) reacting a compound of formula III with an amine, or combination of amines, and a trifluoromethanesulfonylation reagent or luorosulfonylation reagent, to yield a compound of formula IV:

IV wherein $R_1$ and P are defined above and $R_4$ is Tf or $SO_2F$;

step (3) reacting a compound of formula IV in the presence of a catalyst, $(R_3)_3SnCH_2OP''$, and optionally a phosphine ligand, wherein: $R_3$ represents a $C_{1-4}$ lower alkyl, and P'' represents H or a protecting group; to yield the compound of formula I. A preferred process is realized when a phosphine ligand is employed.

A Lewis acid may also be added to the reaction mixture at this third step as an optional reagent. A preferred process is realized when a Lewis acid is employed. Suitable Lewis acids for the first and third steps in the process include, independently, $ZnBr_2$, $ZnCl_2$, $MgCl_2$, $MgBr_2$, $CaCl_2$, and $CaBr_2$. Preferably, $ZnCl_2$ is used as the Lewis acid for both steps.

Some of the intermediates of the present invention occur as geometric isomers. The process of synthesizing all such isomers is encompassed by the present invention.

In a preferred aspect of this invention, $R_1$ is methyl and $R_2$ is $C_{1-12}$ alkyl.

In another preferred aspect of this invention a process for preparation of a compound of formula I:

I wherein P represents TMS, TES or TBS;

comprising refluxing a compound of formula II:

II wherein P is defined above;
in the presence of $ZnCl_2$ and to yield a compound of formula III:

wherein P is defined above;
reacting a compound of formula III in the presence of DIEPA or 2,2,6,6-tetramethylpiperidine, or a combination thereof, and Tf$_2$O, to yield a compound of formula IV:

wherein P and is defined above;
reacting compound IV in the presence of a ZnCl$_2$, Pd(dba)$_2$, and (R$_3$)$_3$SnCH$_2$OP″, wherein:
R$_3$ represents a C$_{1-4}$ lower alkyl, and P″ represents H, TMS, TES, or TBS;
to yield the compound of formula I is described.

The instant invention is generally carried out under an inert atmosphere using nitrogen or argon, preferrably argon.

The invention is described herein in detail, using the terms defined below unless otherwise specified.

pNB refers to the p-nitrobenzyl, represented by the following formula:

Tf refers to triflate (trifluoromethanesulfonyl).

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991).

Examples of suitable protecting groups are: t-butylmethylphenylsilyl, t-butyldiphenylsilyl, trimethylsilyl (TMS), triethylsilyl (TES), t-butyldimethylsilyl (TBS), o-nitrobenzyloxycarbonyl, p-nitrobenzyloxycarbonyl (pNZ), p-nitrobenzyl (pNB), benzyloxycarbonyl, t-butyloxycarbonyl, 2,2,2-trichloroethyloxycarbonyl and allyloxycarbonyl. Preferred protecting groups are TMS, TES and TBS.

Suitable solvents include: N,N-dimethyl formamide (DMF), toluene, tetrahydrofuran, and dichloromethane, hexamethylphosphoramide (HMPA), 1-methyl-2-pyrrolidinone (NMP), 1-ethyl-2-pyrrolidinone (NEP), 1,3-dimethyl-3,4,5, 6-tetrahydro-2(1H)-pyrimidinone (DMPU), 1,3-dimethyl-2-imidazolindinone. Preferable solvents are dichloromethane, HMPA, DMF, NMP, NEP, DMPU or a combination thereof.

Suitable catalysts include rhodium and palladium catalysts such as Pd(O) and Pd(II) complexes, such as PdCl$_2$, Pd(OAc)$_2$, Pd(dba)$_2$, Pd$_2$(dba)$_3$-CHCl$_3$, Rh(II) complexes, Rh(OAc)$_2$, Rh(CO$_2$C$_{1-8}$ alkyl), wherein "dba" represents dibenzylideneacetone. Preferably, the catalyst include Pd(II) complexes, and Rh(II) complexes and more preferably are Pd(dba)$_2$ or Pd(OAc)$_2$.

Suitable phosphine ligands include: 1,3-bis (diphenylphosphino)propane (DPPP); 1,2-bis (diphenylphosphino)-ethane (DPPE); 1,1'-bis (diphenylphosphino)ferrocene (DPPF); or PR$^a$R$^b$R$^c$, wherein R$^a$, R$^b$, and R$^c$ represent, independently:

In a preferred aspect of the invention, the phosphine ligand employed is:

Suitable trifluoromethanesulfonylation reagents include: trifluoromethanesulfonic (triflic) anhydride (Tf$_2$O), trifluoromethanesulfonyl chloride (TfCl), and N-phenyltrifluoromethanesulfonimide. Suitable fluorosulfonylation reagents include S$_2$O$_5$F$_2$. Preferably, Tf$_2$O is the reagent employed.

Suitable amines include triethylamine (TEA), diisopropylethylamine (DIEPA), 2,2,6,6-tetramethylpiperidine, diethylamine, diisopropylamine and t-butylamine. Preferably, the amine chosen is DIEPA or 2,2,6,6-tetramethylpiperidine or a combination thereof.

In another preferred aspect of this invention a compound of formula I which is useful in the synthesis of a variety of carbapenem antibiotics is described:

wherein:
$R_1$ represents $CH_3$ or H; and P and P' independently represent H or a protecting group.

A preferred compound is realized when P represents TES, P' represents H, and $R_1$ represents $CH_3$.

Another preferred compound is realized when P represents TES, P' represents H, and $R_1$ represents H.

Figure 1:
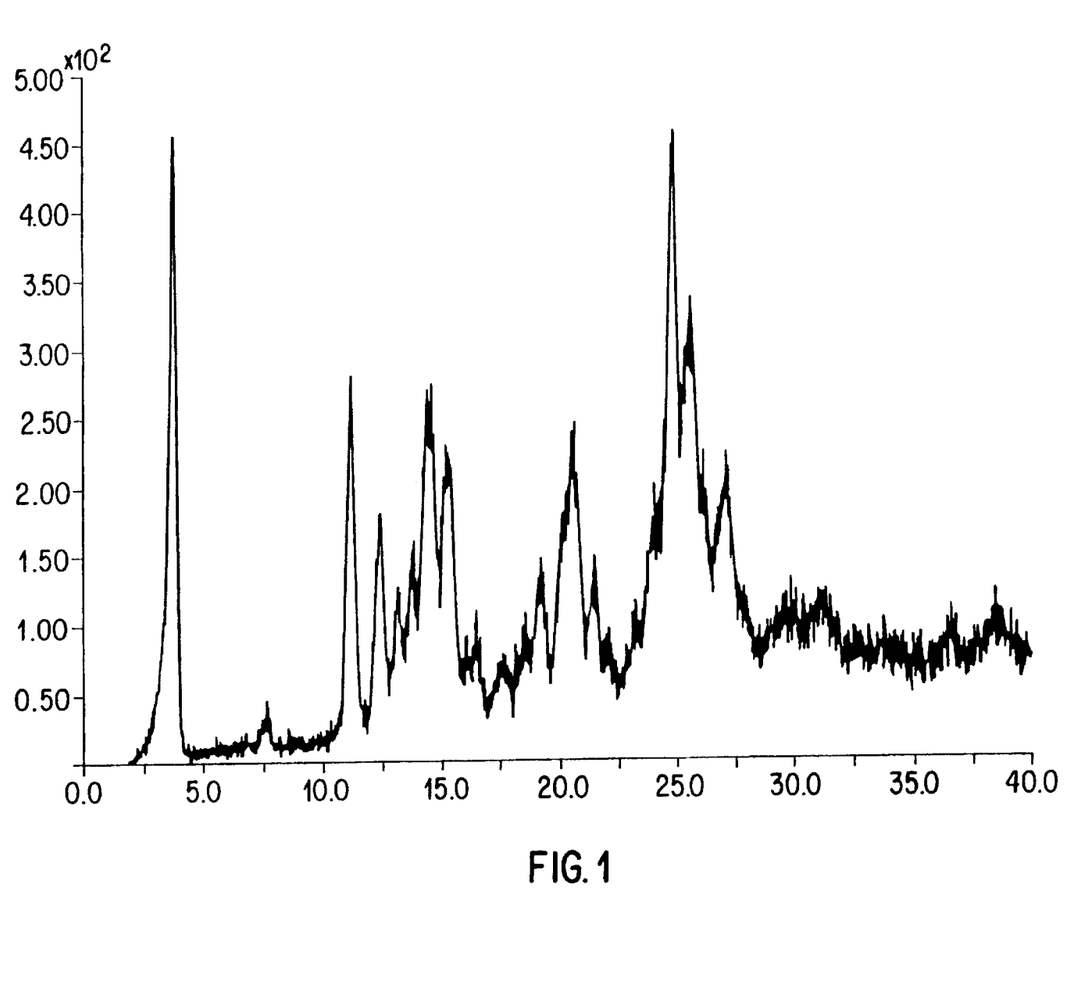
FIG. 1: X-ray crystallography pattern of compound Ia.
Figure 2:
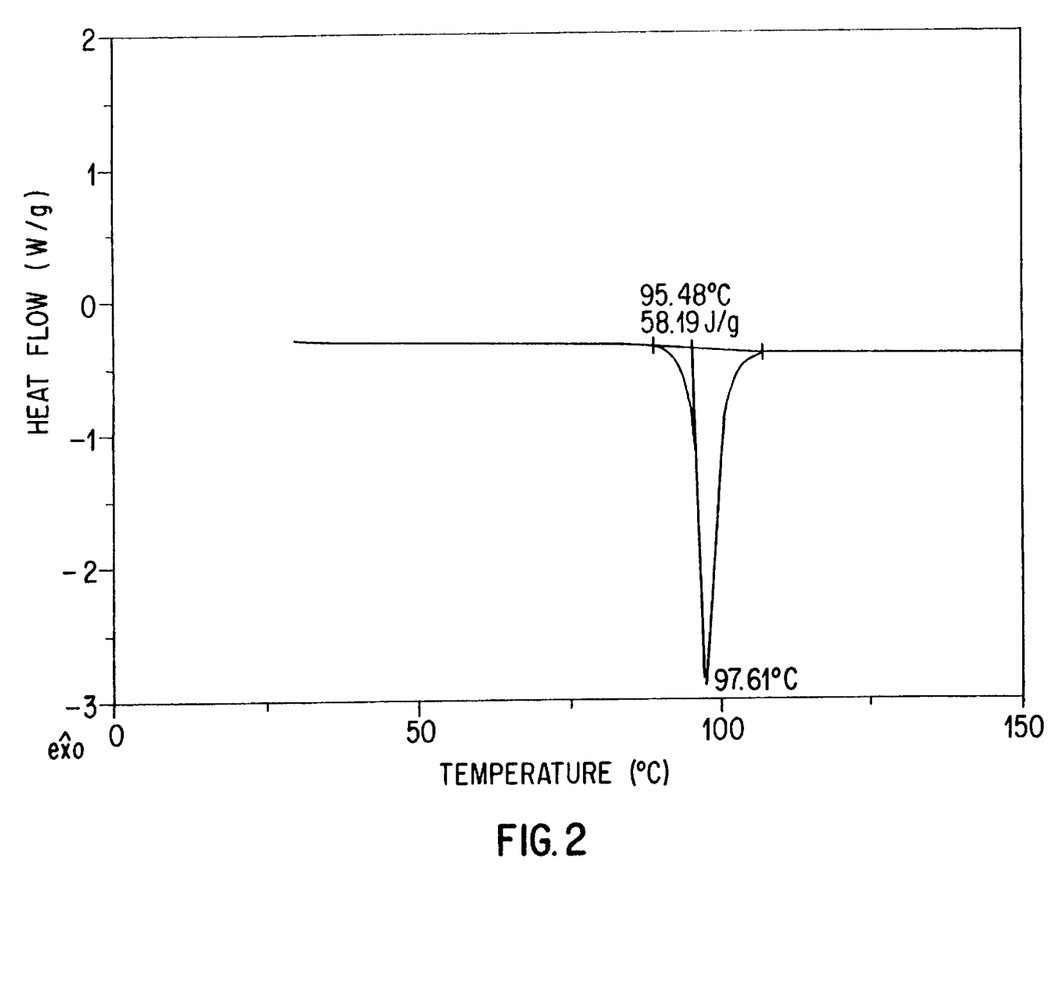
FIG. 2: Differential Scanning Calorimetric Cell (DSC) thermogram of compound Ia.

In another preferred aspect of this invention, the crystalline compound is:

The compounds of the present invention may be isolated in various crystal forms, such as that illustrated by FIGS. 1 and 2. This encompasses compounds of stable crystal structure, and is not limited to the crystal form described in the example.

The present invention is illustrated by the following non-limiting example.

EXAMPLE

Synthesis of Compound Ia

To a 72 L round bottom flask equipped with a mechanical stirrer, an argon inlet, a reflux condenser and a thermocouple was added compound 11 (2.7 Kg) and methylene chloride (13.5 L). Rhodium Octanonate (21.4 g) and zinc chloride (10.7 g) were added to the solution The solution was slowly heated to reflux (nitrogen is evolved during the course of reaction). The solution was refluxed for two hours and then cooled to room temperature. The HPLC assay indicated that the starting material had been consumed. The solution was stored overnight under argon.

The reaction mixture was cooled with a dry ice acetone bath to –50° C. Tetramethylpiperidine (910 mL) and diisopropylethylamine (326 mL) were added over 15 minutes keeping temperature below –40° C. Triflic anhydride (990 mL) was then added over 30 minutes keeping temperature below –40° C. The resulting solution was aged at –50° C. for one hour. HMPA (5.35 L) was added. The solution was then warmed to 20° C. under vacuum for one hour to remove methylene chloride. $Bu_3SnCH_2OH$ (88 wt % pure; 6 L) was added to this dark solution.

To a separate 72 L round bottom flask equipped with a mechanical stirrer, an argon inlet, and a thermocouple was added HMPA (16 L). Tri-2-furyl-phosphine (400 g), $Pd(dba)_2$ (400 g) and zinc chloride (730 g) was added to the HMPA and then heated to 70° C. The enol triflate solution from above was transferred to the catalyst solution over 60 minutes at 70° C. After the addition was completed the reaction was aged at 70° C. for one hour. All operations were carried out under argon.

The reaction mixture was cooled to room temperature. The reaction mixture was pumped into a extractor containing cold MTBE (20 L) and the reaction flask was rinsed with a additional MTBE (15 L). Cold water (35 L) was pumped into the extractor and the two phase solution was agitated for 10 minutes. The layers were allowed to separate and the organic layer was washed with cold water (35 L). The organic layer was separated and concentrated under vacuum. The concentrate was diluted with heptane and loaded on a silica gel column and eluted with EtOAc/Heptane. The fractions, containing the desired compound, were collected and concentrated, and the product crystallized during concentration. The solids were collected and dried (1.53 Kg; 79.5 wt %; 46.5 isolated yield).

Analytically pure material was obtained by silica gel column chromatography (EtOAc/Heptane), and subsequent crystallization from heptane. The melting point was measured using DSC thermography. The DSC instrument was a TA Instrument DSC 9210 and the DSC curve run at a heating rate of 10° C./min under a nitrogen flow of about 30 mL/min from room temperature to 250° C. A single endotherm (melting endotherm) was detected with a peak temperature of 98° C., an extrapolated onset temperature of 95° C. and a heat of melting of 58 Joules/gm. (See FIG. 2).

NMR spectroscopy yielded the following results: $^1H$ NMR ($CDCl_3$, 250 MHz) δ 8.22 (m, 2H), 7.64 (d, J=8.7 Hz, 2H), 5.47 (AB d, J=13.9 Hz, 1H), 5.27 (AB d, J=13.9 Hz, 1H), 4.54 (AB dd, J=14.9, 6.6 Hz, 1H), 4.38 (AB dd, J=14.9, 5.9 Hz, 1H), 4.25 (m, 1H), 4.22 (dd, J=7.0, 3.0 Hz, 1H), 3.27 (dd, J=5.7, 3.0 Hz, 1H), 3.24 (m, 1H), 3.09 (m, 1H), 1.26 (d, J=6.2 Hz, 3H), 1.21 (d, J=7.4 Hz, 3H), 0.94 (t, J=7.9 Hz, 9H), 0.59 (m, 6H). $^{13}C$ NMR ($CDCl_3$, 63 MHz) δ 175.1, 161.8, 153.5, 147.6, 142.4, 128.0, 127.3, 123.7, 65.8, 65.6, 60.3, 57.6, 55.9, 41.6, 22.5, 15.3, 6.7, 4.9.

The X-ray crystallography was conducted using a Phillips APD3720 using CuKa radiation. The powder pattern was run at 0.075 2-θ/sec from about 2 to about 40 2-θ. The x-ray crystallography pattern ielded the results summarized in FIG. 1 and Table 1, below.

TABLE 1

| Peak Angle (°) | d-spacing (Å) | Relative Intensity (%) |
|---|---|---|
| 3.8 | 23.3 | 100 |
| 7.7 | 11.5 | 6 |
| 11.3 | 7.85 | 56 |
| 12.5 | 7.08 | 38 |
| 13.2 | 6.69 | 22 |
| 13.8 | 6.41 | 28 |
| 14.5 | 6.11 | 57 |
| 18.5 | 4.79 | 11 |
| 19.1 | 4.64 | 18 |
| 20.6 | 4.31 | 43 |
| 21.5 | 4.12 | 19 |
| 24.9 | 3.57 | 89 |
| 25.6 | 3.84 | 56 |
| 27.1 | 3.29 | 30 |
| 29.5 | 3.02 | 6 |
| 31.2 | 2.87 | 9 |
| 36.5 | 2.46 | 6 |
| 38.4 | 2.34 | 7 |

What is claimed is:

1. A process for preparation of a compound of formula I:

wherein:

$R_1$ represents $CH_3$ or H; and P represents a protecting group;

comprising reacting a compound of formula IV:

wherein pNB represents p-nitrobenzyl, $R_1$ and P are defined above and $R_4$ represents Tf (when $R_4$ is Tf, —$OR_4$ is triflate) or $SO_2F$;

in the presence of a catalyst and $(R_3)_3SnCH_2OP'''$, wherein: each $R_3$ represents $C_{1-4}$ lower alkyl, and P''' represents H or a protecting group, to yield the compound of formula I.

2. A process according to claim 1 further comprising adding a Lewis acid selected from the group consisting of $ZnBr_2$, $ZnCl_2$, $MgCl_2$, $MgBr_2$, $CaCl_2$ and $CaBr_2$.

3. A process according to claim 2 wherein the Lewis acid is $ZnCl_2$.

4. A process according to claim 1 further comprising adding a phosphine ligand selected from the group consisting of: 1,3-bis(diphenylphosphino)-propane (DPPP); 1,2-bis(diphenylphosphino)-ethane (DPPE); 1,1'-bis(diphenylphosphino)ferrocene (DPPF); and $PR^aR^bR^c$, wherein $R^a$, $R^b$, and $R^c$ represent, independently:

5. A process in accordance with claim 4 wherein the phosphine ligand is:

6. A process according to claim 1 wherein the catalyst is selected from the group consisting of Pd(II) complexes, and Rh(II) complexes.

7. A process in accordance with claim 6 wherein the Palladium catalyst is selected from the group consisting of Pd(dibenzylideneacetone)$_2$ and Pd(acetate)$_2$.

8. A process in accordance with claim 1 wherein the protecting group P is selected from the group consisting of t-butylmethyl-phenylsilyl, t-butyldiphenylsilyl, trimethylsilyl (TMS), triethylsilyl (TES), t-butyldimethylsilyl (TBS), o-nitrobenzyloxycarbonyl, p-nitrobenzyloxycarbonyl (pNZ), p-nitrobenzyl (pNB), benzyloxy-carbonyl, t-butyloxycarbonyl, 2,2,2-trichloroethyloxycarbonyl and allyloxycarbonyl.

9. A process in accordance with claim 8 wherein the protecting group is TMS, TES or TBS.

10. A process according to claim 1 wherein $R_1$ is methyl.

11. A process according to claim 1 which is carried out under inert conditions.

12. A process according to claim 11 wherein the inert condition comprises using nitrogen or argon.

13. A process for preparation of a compound of formula I:

-continued wherein R₁ represents CH₃ and P represents triethylsilyl, trimethylsilyl or t-butyldimethylsilyl; comprising:

reacting a compound of formula IV:

wherein P and R₁ are defined above and Tf represents triflate;
in the presence of ZnCl₂, Pd(dibenzylideneacetone)₂, and $(R_3)_3SnCH_2OP''$, wherein:
R₃ represents a $C_{1-4}$ lower alkyl, and P'' represents H, triethylsilyl, trimethylsilyl or t-butyldimethylsilyl; to yield the compound of formula I, said process conducted under inert conditions using nitrogen or argon.

14. A process for preparation of a compound of formula I:

wherein P represents triethylsilyl, trimethylsilyl or t-butyldimethylsilyl;

comprising refluxing a compound of formula II:

wherein P is defined above;
in the presence of ZnCl₂ and to yield a compound of formula III:

wherein P is defined above;
reacting a compound of formula III in the presence of diisopropylethylamine or 2,2,6,6-tetramethylpiperidine, or a combination thereof, and trifluoromethanesulfonic anhydride, to yield a compound of formula IV:

wherein P is defined above and OTf is triflate;
reacting compound IV in the presence of a ZnCl₂, Pd(dibenzylideneacetone)₂, and $(R_3)_3SnCH_2OP''$, wherein R₃ represents a $C_{1-4}$ lower alkyl, and
P'' represents H, triethylsilyl, trimethylsilyl or t-butyldimethylsilyl; to yield the compound of formula I, said process conducted under inert conditions using nitrogen or argon.

15. A compound of the formula:

16. A compound of the formula:

17. A crystalline compound of the formula:

wherein TES is triethylsilyl.

18. The cystalline compound in accordance with claim 17 having an X-ray crystallography pattern of FIG. 1.

19. A crystalline compound of the formula:

wherein TES is triethylsilyl, exhibiting a DSC thermogram as shown in FIG. 2.

20. A process for preparation of a compound of formula I:

wherein:
pNB represents p-nitrobenzyl;
$R_1$ represents $CH_3$ or H;

and P is a protecting group selected from the group consisting of t-butylmethylphenylsilyl, t-butyldiphenylsilyl, trimethylsilyl, triethylsilyl, t-butyldimethylsilyl, o-nitrobenzyloxycarbonyl, p-nitrobenzyloxycarbonyl, p-nitrobenzyl, benzyloxycarbonyl, t-butyloxycarbonyl, 2,2,2-trichloroethyloxycarbonyl and allyloxycarbonyl;
comprising:
step (1) heating a compound of formula II:

wherein $R_1$ and P are defined above;
in the presence of wherein $R_2$ is $C_{1-15}$ alkyl, to yield a compound of formula III:

wherein $R_1$ and P are defined above;
step (2) reacting a compound of formula III in the presence of an amine selected from the group consistng of triethylamine, diisopropylethylamine, 2,2,6,6-tetramethylpiperidine, diisopropylamine, t-butylamine and diethylamine, and a trifluoromethanesulfonylation reagent or fluorosulfonylation reagent, to yield a compound of formula IV:

wherein $R_1$ and P and are defined above, and $R_4$ represents Tf or $SO_2F$;
step (3) reacting compound IV in the presence of a catalyst selected from the group consisting of Pd(II) complexes, $Rh(CO_2C_{1-8}$ alkyl) and Rh(II) complexes, and $(R_3)_3SnCH2OP"$, wherein each $R_3$ represents $C_{1-4}$ lower alkyl and P" represents H or a protecting group, to yield the compound of formula I.

21. The process according to claim 20 wherein the protecting group is selected from the group consisting of trimethylsilyl, triethylsilyl and t-butyldimethylsilyl.

22. A claim according to claim 6 wherein the Pd(II) catalyst are selected from the group consisting of $PdCl_2$, $Pd(acetate)_2$, $Pd(dibenzylideneacetone)_2$, and $Pd_2(dibenzylideneacetone)_3$—$CHCl_3$, and the Rh(II) catalyst is $Rh(acetate)_2$.

* * * * *